United States Patent
Kasuya

(10) Patent No.: US 7,447,293 B2
(45) Date of Patent: Nov. 4, 2008

(54) X-RAY COMPUTER TOMOGRAPHIC IMAGING APPARATUS AND CONTROL METHOD THEREOF

(75) Inventor: Yuichi Kasuya, Otawara (JP)

(73) Assignees: Kabushiki Kaisha Toshiba, Tokyo (JP); Toshiba Medical Systems Corporation, Otawara-shi (JP)

(*) Notice: Subject to any disclaimer, the term of this patent is extended or adjusted under 35 U.S.C. 154(b) by 239 days.

(21) Appl. No.: 11/276,784

(22) Filed: Mar. 14, 2006

(65) Prior Publication Data

US 2006/0210013 A1    Sep. 21, 2006

(30) Foreign Application Priority Data

Mar. 15, 2005   (JP)   ............... 2005-073894

(51) Int. Cl.
  *A61B 6/03*   (2006.01)
(52) U.S. Cl. .................. 378/4; 378/103
(58) Field of Classification Search ............ 378/4, 378/15, 103, 197
  See application file for complete search history.

(56) References Cited

U.S. PATENT DOCUMENTS

| | | | | |
|---|---|---|---|---|
| 4,181,857 A | * | 1/1980 | Miyoshi | 378/103 |
| 4,200,797 A | * | 4/1980 | Bax | 378/15 |
| 5,226,064 A | * | 7/1993 | Yahata et al. | 378/4 |
| 6,169,782 B1 | * | 1/2001 | Zetterlund | 378/103 |
| 2004/0196955 A1 | | 10/2004 | Kasuya | |

FOREIGN PATENT DOCUMENTS

| | | |
|---|---|---|
| JP | 9-56710 | 3/1997 |
| JP | 9-276262 | 10/1997 |
| JP | 2002-336236 | 11/2002 |
| JP | 2004-215741 | 8/2004 |

\* cited by examiner

*Primary Examiner*—Chih-Cheng G Kao
(74) *Attorney, Agent, or Firm*—Oblon, Spivak, McClelland, Maier & Neustadt, P.C.

(57) ABSTRACT

An X-ray CT apparatus according to this invention comprises X-ray generating unit which irradiates X rays toward a object, detecting unit which detects X rays irradiated from the X-ray generating unit and passed through the object, support unit which supports the X-ray generating unit and the detecting unit, driving unit which rotates the support unit, and control unit which controls the driving unit, accumulates regenerative energy generated when the rotating speed of the support unit is decelerated, and supplies the accumulated regenerative energy to the driving unit to rotate the support unit.

18 Claims, 9 Drawing Sheets

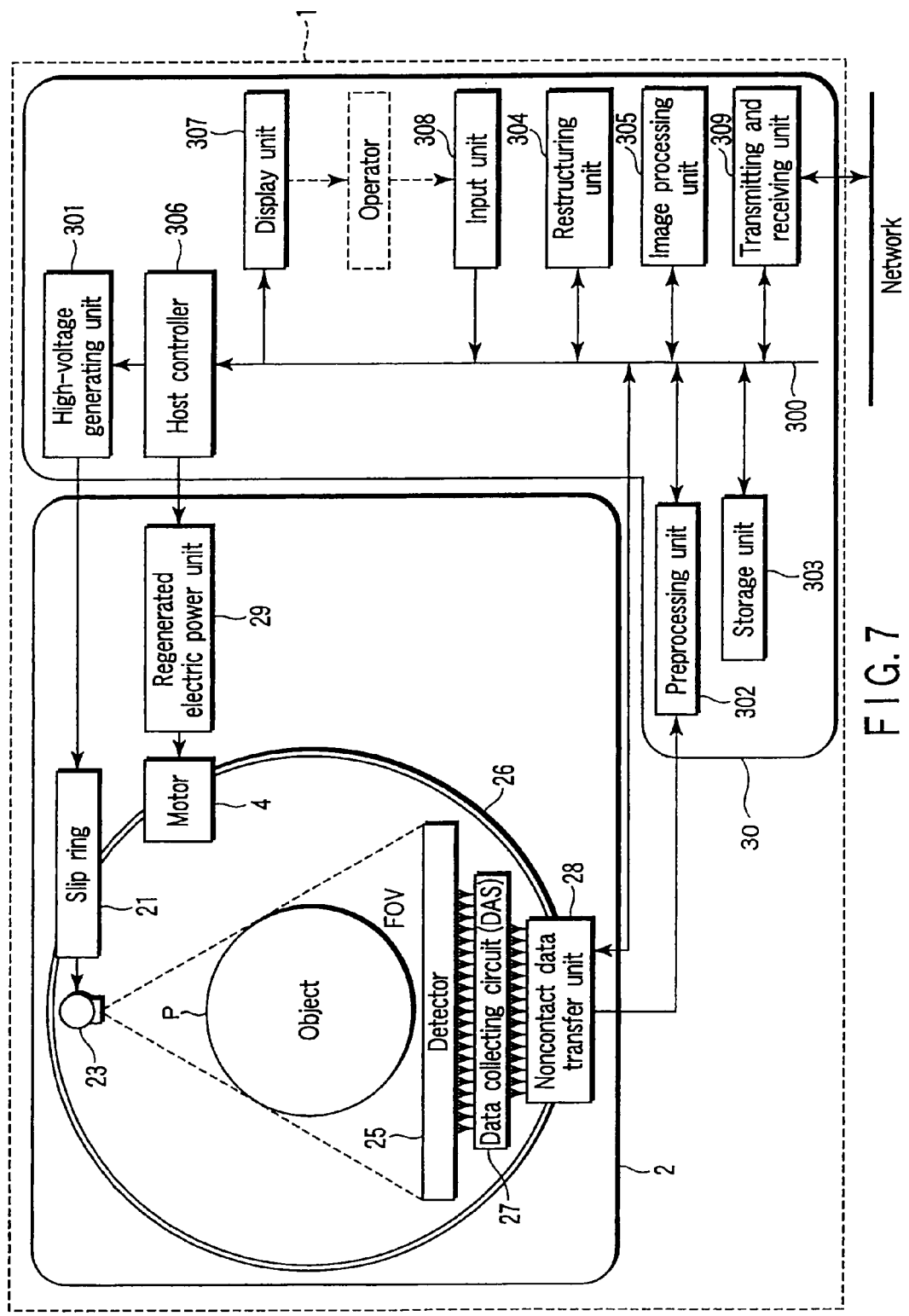
F I G. 7

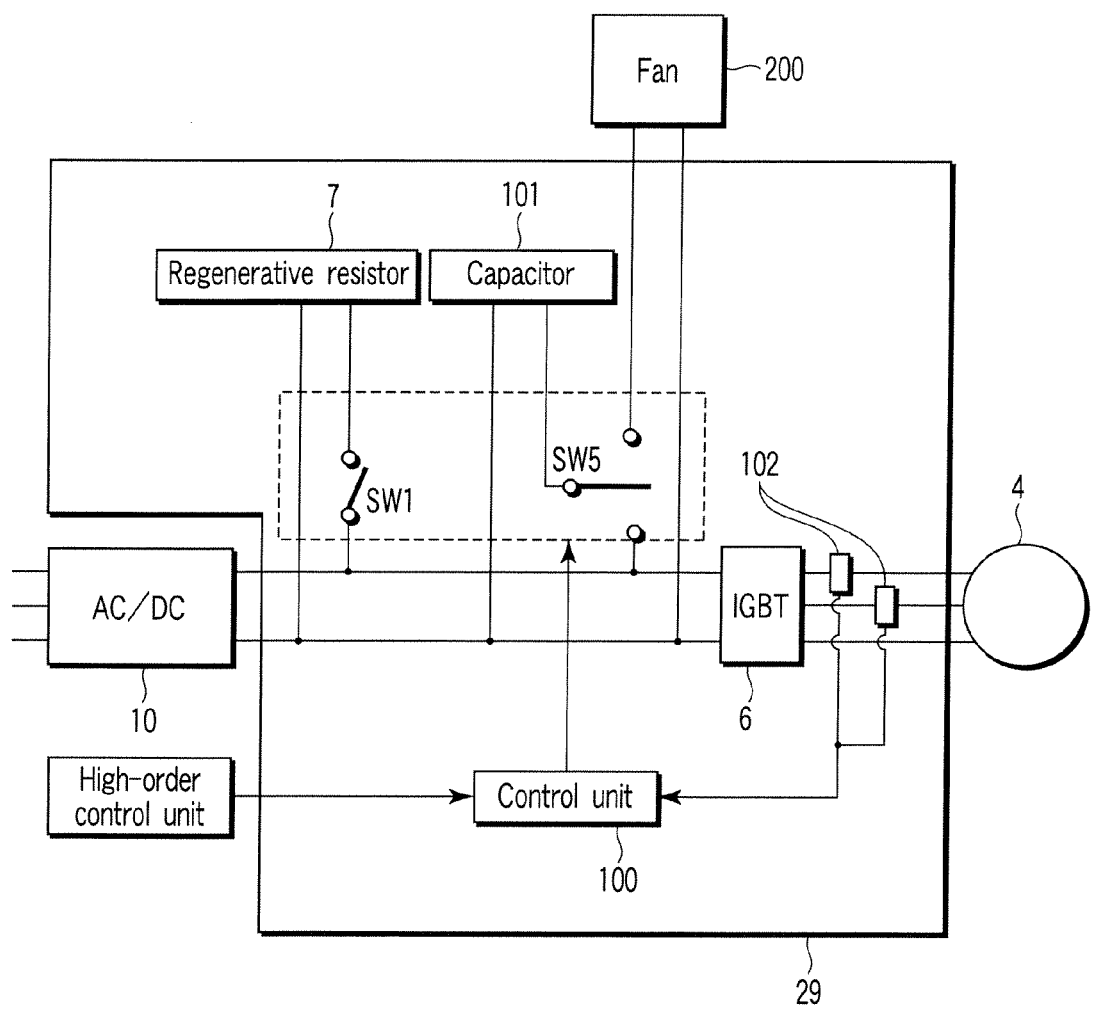
F I G. 10

X-RAY COMPUTER TOMOGRAPHIC IMAGING APPARATUS AND CONTROL METHOD THEREOF

CROSS-REFERENCE TO RELATED APPLICATIONS

This application is based upon and claims the benefit of priority from prior Japanese Patent Application No. 2005-073894, filed Mar. 15, 2005, the entire contents of which are incorporated herein by reference.

BACKGROUND OF THE INVENTION

1. Field of the Invention

The present invention relates to an X-ray computer tomographic imaging apparatus and control method thereof.

2. Description of the Related Art

Recent advances in medical diagnostic apparatuses are remarkable. Especially in the field of X-ray computer tomographic imaging apparatuses (X-ray CT apparatuses) that get tomographic images of a object using X-rays, various efforts have been made constantly by, for example, diversifying their applications or shortening the photographing time.

In parallel with such progressive technical innovations, the problem of how to dissipate heat generated collaterally in the apparatus to the outside has always been considered. However, the more the performance or function of the apparatus is improved, the more the amount of heat to be dissipated increases, with the result that the problem hangs heavy.

Typical heat generated in the X-ray CT apparatus is attributable to a regenerative resistor. A regenerative resistor is a resistive member provided to convert into heat energy the energy of back electromotive force generated in decelerating the rotation of a motor (such as a direct drive motor or a rotation servo motor) for driving the rotating frame to get tomographic images of a object while rotating. Therefore, when the motor is accelerated and decelerated frequently, for example, when a large number of people are photographed consecutively, or when a service engineer does maintenance, the regenerative resistor may reach a considerable temperature (about 70 degrees). Known configurations to deal with such a situation include not only the one that simply has an increased number of regenerative resistors but also, for example, the ones explained below.

The gantry of some X-ray CT apparatuses have a rectangular appearance when viewed from the front. Such X-ray CT apparatuses often employ the following configuration: a regenerative resistor is provided in the upper part of the gantry in such a manner that it is arranged so that heat may easily dissipate outside the apparatus and is brought into contact with the sheet metal in the gantry to allow heat to escape from the sheet metal.

In recent years, an X-ray CT apparatus has been popularized which has the upper part of the gantry formed into a round shape to give the apparatus a soft image in order to wipe away the mechanical image of the apparatus, thereby relieving discomfort the object undergoes. In such an X-ray CT apparatus, since it is difficult to secure a sufficient space to arrange a regenerative resistor in the upper part, a regenerative resistor is often provided on the apparatus side.

The aforementioned X-ray CT apparatus uses as an additional configuration element a fan or the like to guide heat generated by a regenerative resistor to the outside. For example, Jpn. Pat. Appln. KOKAI Publication No. H9-276262 mentioned below has disclosed an X-ray CT apparatus which has a suction opening made in the upper part of the photographic opening and a cooling fan provided in the upper part of the apparatus to generate an airflow inside the apparatus, thereby dissipating heat.

In addition, Jpn. Pat. Appln. KOKAI Publication No. H9-56710 mentioned below has disclosed an X-ray CT apparatus (computerized traverse axial tomography) which is configured to arrange a plurality of blade members at a support member and rotate the blade members together with a gantry rotating unit to send air, thereby dissipating heat from inside the apparatus. Like the configuration of Jpn. Pat. Appln. KOKAI Publication No. H9-276262, the configuration of Jpn. Pat. Appln. KOKAI Publication No. H9-56710 is such that it dissipates heat by keeping good ventilation inside the apparatus.

Furthermore, Jpn. Pat. Appln. KOKAI Publication No. 2002-336236 described below has disclosed an X-ray CT scanning system which includes a regenerative resistor unit provided in a gantry apparatus (X-ray CT apparatus) and a blower fan that transfers the heat generated by the regenerative resistor unit to the top board of the carrier unit on which the object is laid. In the X-ray CT scanning system, heating the top board makes it possible to warm up the object. In this case, too, a method of cooling the regenerative resistor by airflow is used.

Here, as an example, a conventional X-ray CT apparatus which has a configuration that dissipates heat through a regenerative resistor will be explained below using drawings. FIG. 1 is a perspective front view schematically showing the configuration of a conventional X-ray CT apparatus. FIG. 2 is a block diagram showing the configuration of the conventional X-ray CT apparatus. As shown in FIG. 1, the X-ray CT apparatus 1 is an apparatus which irradiates X rays to a object, while scanning the object, and detects the transmitted X rays. The X-ray CT apparatus 1, a couch for transporting the object laid on the top board to a photographing position (or photographic opening shown below), and a computer for analyzing the detected data from the X-ray CT apparatus 1 and restructuring an X-ray tomogram (neither of which is shown) constitute a tomographic X-ray system.

An opening made near the center of the body 2 of the X-ray CT apparatus 1 forms a photographic opening 3 into which the object laid on the top board is to be inserted. The body 2 houses various devices for irradiating X rays to the object in various directions and detecting the X rays passed through the object. The devices include a motor 4, such as a direct drive motor, a rotating frame 5, and a servo amplifier 6. A regenerative resistor 7 is connected to the servo amplifier 6.

The rotating frame 5, which is a frame provided so as to enclose the photographic opening 3, is rotated by the motor 4. On the rotating frame 5 (support means), an X-ray tube 8 (X-ray generating means) which outputs X rays and a detector 9 (detecting means) which detects X rays output from the X-ray tube 8 are supported in opposed positions. Moreover, the rotating frame 5 is provided with a power unit 10 for supplying electric power to the X-ray tube 8 and the detector 9 and a signal processing unit 11 for processing the result of detection by the detector 9.

The servo amplifier 6 adjusts the voltage and frequency of the electric power supplied to the motor 4 on the basis of a signal transmitted from a control unit, thereby driving and stopping the motor 4 or controlling the rotating speed.

The regenerative resistor 7 is a member for converting electric energy (regenerative energy) generated during the deceleration of the motor and flowing backward into heat energy. A regenerative resistor is also provided in the servo amplifier 6. It is a regenerative resistor 7 that is used to consume the regenerative energy the built-in regenerative resistor cannot deal with. The regenerative resistor 7 is provided in the upper part of the side of the body 2 of the X-ray CT apparatus 1 and is thermally connected to a heat-dissipating member, thereby dissipating heat to the outside.

The individual members arranged as described above constitute a configuration as shown in FIG. 2. As shown in FIG. 2, the power unit 10 is connected to the motor 4 via the servo amplifier 6 composed of an IGBT (Insulated Gate Bipolar Transistor). The regenerative resistor 7 is inserted in the transmission path between the power unit 10 and the IGBT. On the regenerative resistor 7 side, there is provided a switch SW1 controlled by the control unit 100 to send the regenerative energy generated during the deceleration of the motor 4 to the regenerative resistor 7 connected to the heating-dissipating member.

In the X-ray CT apparatus configured as described above, a photographing process by the tomographic X-ray system including the X-ray CT apparatus 1 is basically executed in the following process. The X-ray CT apparatus I not only supplies electric power from the servo amplifier 6 to the motor 4 and rotates the rotating frame 5 but also irradiates X rays from the X-ray tube 8, thereby detecting with the detector 9 the X-rays passed through the object inserted in the photographic opening 3. At this time, the X-ray tube 8 and detector 9 are in operation, receiving the electric power supplied from the power unit 10. The transmitted X rays detected by the detector 9 are processed by the signal processing unit 11, which produces image data and transmits the image data to the computer. Then, the computer restructures the image data into an image, thereby providing a tomogram of the object.

As a result of the repetition of the aforementioned photographing process, as shown in FIG. 3, energy based on back electromotive force during the deceleration of the motor 4 (sensed by the control unit 100 in S11), that is, regenerative energy, is generated in large amounts. When the control unit 100 turns on the switch SW1 (S12), the regenerative energy is sent to the regenerative resistor 7, with the result that the heat-dissipating member thermally connected to the regenerative resistor dissipates heat.

As was mentioned at the beginning, X-ray CT apparatuses are continually making progress and particularly an attempt to reduce the burden on the object by shortening the photographing time is now in progress. To shorten the photographing time, it is necessary to shorten the scanning time. Therefore, it is necessary to rotate the rotating frame at higher speed, that is, to control the motor in high-speed rotation. To realize this, the motor has to be accelerated and decelerated rapidly, resulting in the generation of a large amount of regenerative energy as compared with a conventional equivalent. Thus, the technique for converging a great deal of regenerative energy generated into heat energy efficiently is required. That is, when the simplification of the configuration and manufacturing costs are taken into consideration, the so-called air-cooled heat-dissipating functions described in above undeniably have their limits in dealing with an increase in the dissipation of heat energy resulting from the speeding up of the rotation of the rotating frame. Consequently, it is anxious that various precision instruments will malfunction due to a temperature rise in the apparatus.

BRIEF SUMMARY OF THE INVENTION

It is, accordingly, an object of the present invention to provide an X-ray CT apparatus capable of making efficient use of the regenerative energy accumulated in a regenerative resistor.

According to an aspect of the present invention, there is provided an X-ray computer tomographic imaging apparatus which comprises: a rotating frame which includes an X-ray generating unit to irradiate X rays and an X ray detecting unit to detect X rays and which rotates around a predetermined axis; a first driving unit configured to drive the rotating frame rotationally; a power source which provide electric power to the first driving unit; and a regenerated electric power unit to accumulate regenerative energy generated when the rotating speed of the rotating frame is decelerated.

According to another aspect of the present invention, there is provided a control method of a X-ray computer tomographic imaging apparatus which comprises: driving a rotational body rotationally around a predetermined axis, the rotational body including an X-ray generating unit to irradiate X rays and an X ray detecting unit to detect X rays; and accumulating regenerative energy generated when the rotating speed of the rotating frame is decelerated.

BRIEF DESCRIPTION OF THE SEVERAL VIEWS OF THE DRAWING

FIG. 7 is a block diagram showing the configuration of the X-ray CT apparatus 1 according to the second embodiment;

FIG. 10 is a diagram showing the configuration for performing a regenerative energy recycling function according to the third embodiment;

DETAILED DESCRIPTION OF THE INVENTION

Figure 1:
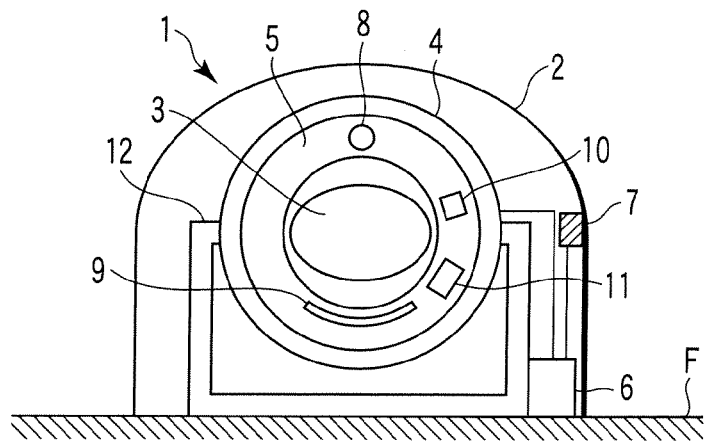
FIG. 1 is a perspective front view schematically showing the configuration of a conventional X-ray CT apparatus.

Hereinafter, referring to the accompanying drawings, a first to a fourth embodiment of the present invention will be explained. In the explanation below, component elements having almost the same function and configuration are indicated by the same reference numerals. Repeated explanation will be given only when necessary.

Hereinafter, referring to the accompanying drawings, an X-ray CT apparatus according to a first embodiment of the present invention will be explained in detail.

First Embodiment (Configuration)

Figure 4:
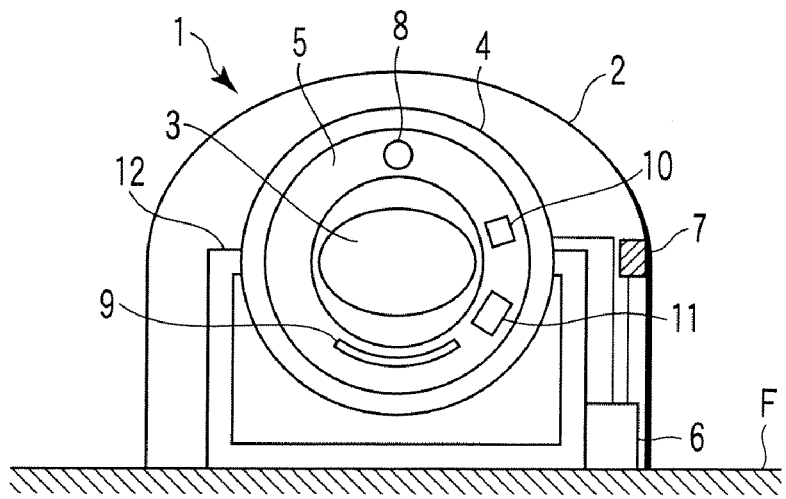
FIG. 4 is a perspective front view schematically showing the configuration of an X-ray CT apparatus according to a first embodiment of the present invention.
Figure 5:
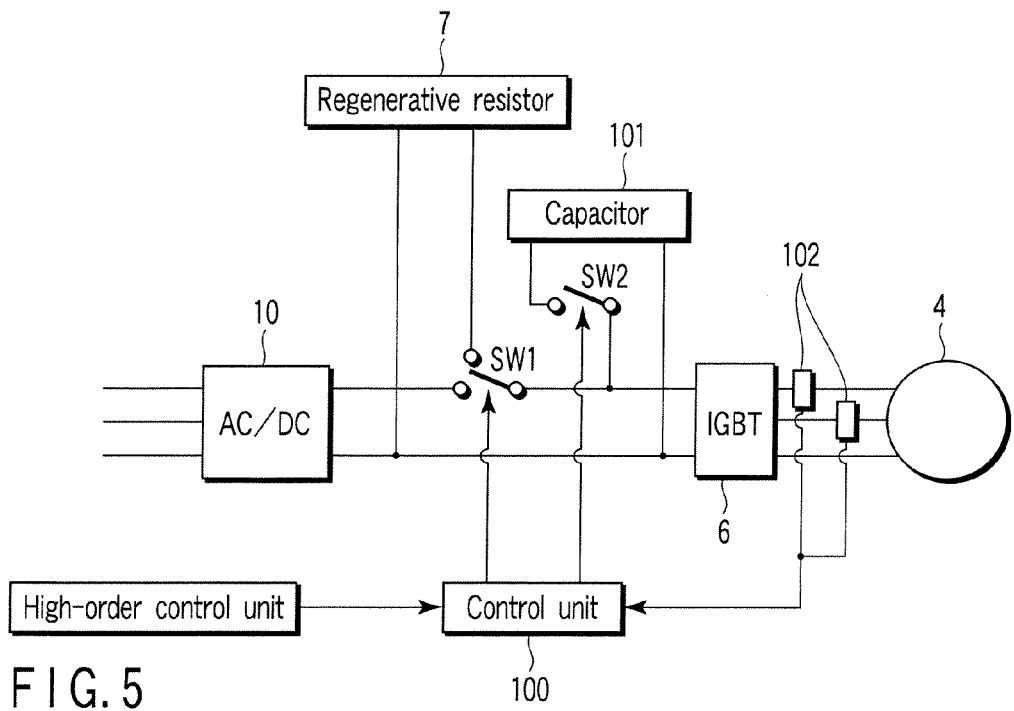
FIG. 5 is a block diagram showing the configuration of the X-ray CT apparatus according to the first embodiment.

FIG. 4 is a perspective front view schematically showing the configuration of an X-ray CT apparatus 1 installed on the floor F of the photographing room in a hospital or the like. FIG. 5 is a block diagram showing the configuration of the X-ray CT apparatus according to the present invention. As shown in FIG. 4, the X-ray CT apparatus 1 is an apparatus which irradiates a object with X rays, while scanning the object, and detecting the transmitted X rays. The X-ray CT apparatus 1, a couch for transporting the object laid on the top board to a photographing position (or photographic opening shown below), and a computer for analyzing the detected data from the X-ray CT apparatus 1 and restructuring an X-ray tomogram (neither of which is shown) constitute a tomographic X-ray system.

An opening made near the center of the body 2 of the X-ray CT apparatus 1 forms a photographic opening 3 into which the object laid on the top board is to be inserted. The body 2 houses various devices for irradiating X rays to the object in various directions and detecting the X rays passed through the object. The devices include a motor 4, such as a direct drive motor, a rotating frame 5, and a servo amplifier 6. A regenerative resistor 7 is connected to the servo amplifier 6.

The rotating frame 5, which is a frame provided so as to enclose the photographic opening 3, is rotated by the motor 4. On the rotating frame 5 (support means), an X-ray tube 8 (X-ray generating means) which outputs X rays and a detector 9 (detecting means) which detects X rays output from the X-ray tube 8 are supported in opposed positions. Moreover, the rotating frame 5 is provided with a power unit 10 for supplying electric power to the X-ray tube 8 and the detector 9 and a signal processing unit 11 for processing the result of detection by the detector 9.

The servo amplifier 6 adjusts the voltage and frequency of the electric power supplied to the motor 4 on the basis of a signal transmitted from a control unit 100 (control means) shown in FIG. 5, thereby driving and stopping the motor 4 or controlling the rotating speed.

The regenerative resistor 7 is a member for converting electric energy (regenerative energy) generated during the deceleration of the motor 4 and flowing backward into heat energy and consuming the heat energy. A regenerative resistor is also provided in the servo amplifier 6. It is a regenerative resistor 7 that is used to consume the regenerative energy the built-in regenerative resistor cannot deal with. Like a conventional equivalent, the regenerative resistor 7 of the embodiment is provided in the upper part of the side of the body 2 of the X-ray CT apparatus 1.

Figure 2:
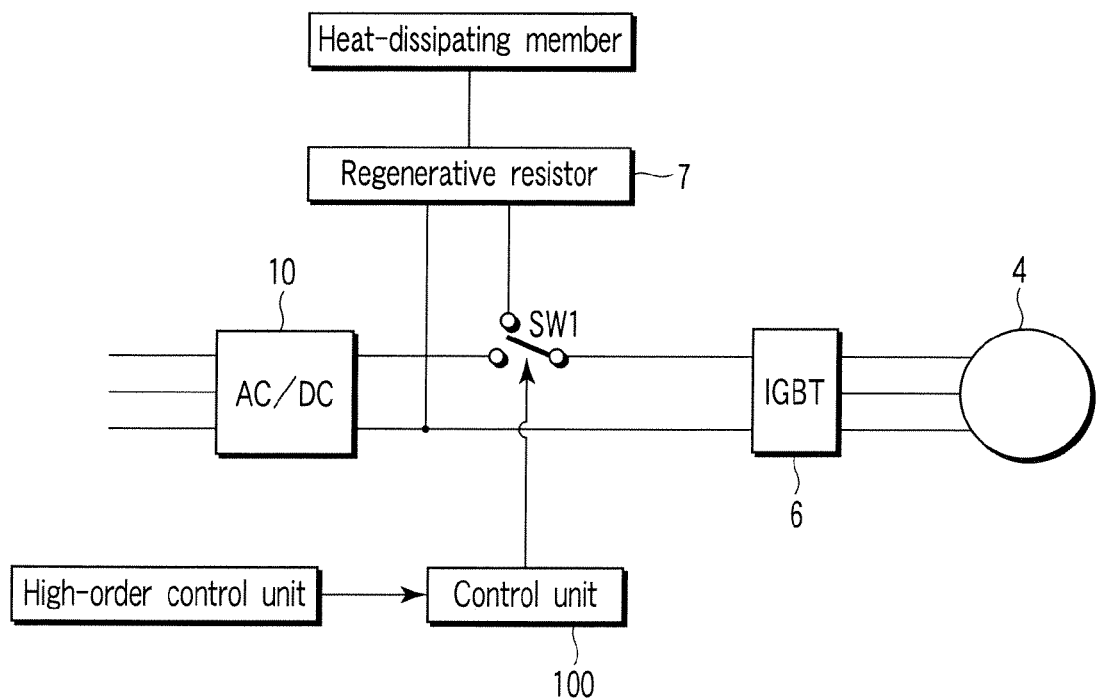
FIG. 2 is a block diagram showing the configuration of the conventional X-ray CT apparatus.
Figure 3:
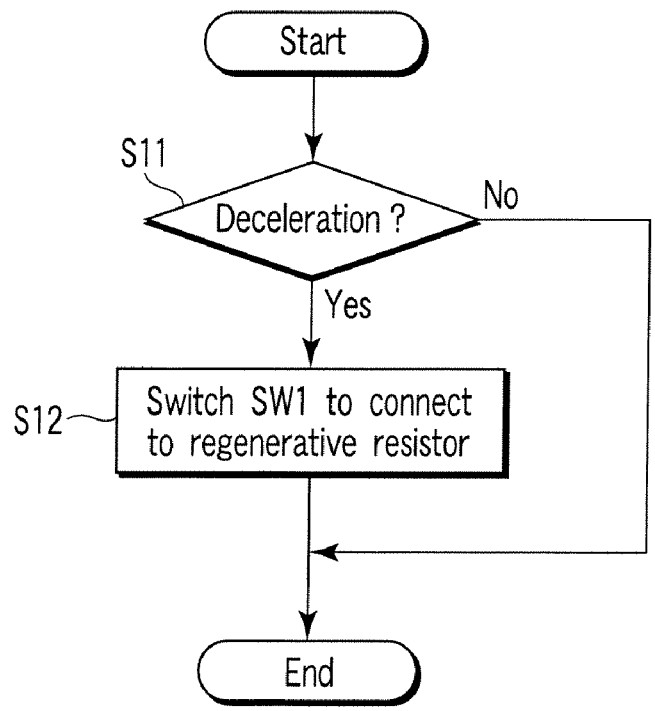
FIG. 3 is a flowchart to help explain the operation of the conventional X-ray CT apparatus.

The individual members arranged as described above constitute a configuration as shown in FIG. 2. As shown in FIG. 2, the power unit 10 is connected to the motor 4 via the servo amplifier 6 composed of an IGBT. The regenerative resistor 7 and a charging capacitor 101 are inserted in the transmission path between the power unit 10 and the IGBT. On the regenerative resistor 7 side, there is provided a switch SW1 controlled by the control unit 100 to accumulate the regenerative energy generated during the deceleration of the motor 4 via the regenerative resistor 7 in the charging capacitor 101. Furthermore, there is provided a switch SW2 controlled by the control unit 100 to supply the regenerative energy accumulated in the charging capacitor 101 via the IGBT to the motor 4.

Moreover, in the transmission path connecting the IGBT and the motor 4, there is provided a current detecting unit 102 for detecting the value of the current in the transmission path, more specifically, detecting an instantaneous power failure. When detecting an instantaneous power failure in the transmission path, the current detecting unit 102 gives a response sufficiently faster than the time of the instantaneous power failure (e.g., several milliseconds) to the control unit 100. Specifically, the switch SW2 is a switch turned on by the control unit 100 informed that the current detecting unit 102 has detected an instantaneous power failure. The time required for the switch SW2 to be turned on since the current detecting unit 102 detected the instantaneous power failure is assumed to be sufficiently shorter than the time of the instantaneous power failure.

(Operation)

Figure 6:
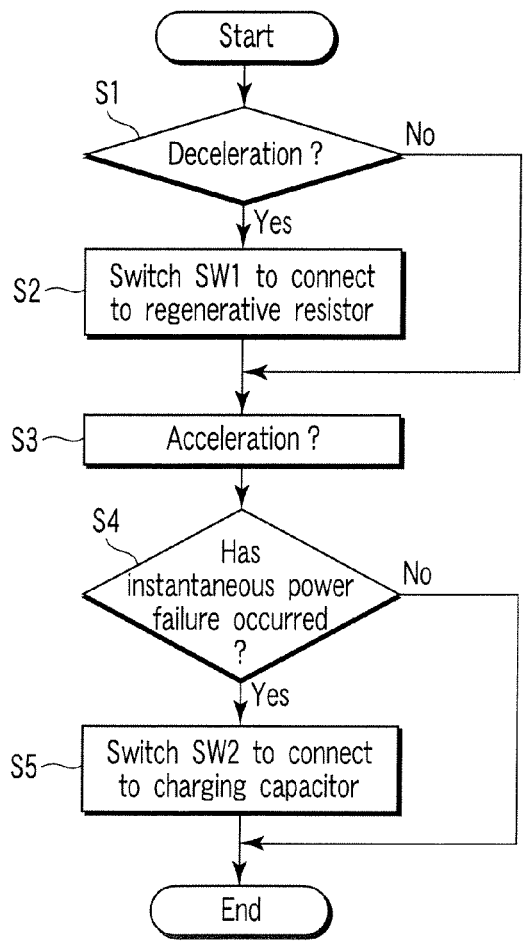
FIG. 6 is a flowchart to help explain the operation of the X-ray CT apparatus according to the first embodiment.

Hereinafter, the operation of the X-ray CT apparatus 1 configured as described above will be explained with reference to FIG. 6.

First, a photographing process by the tomographic X-ray system including the X-ray CT apparatus 1 is basically executed in the following process. The X-ray CT apparatus 1 not only supplies electric power from the servo amplifier 6 to the motor 4 to rotate the rotating frame 5 but also irradiates X rays from the X-ray tube 8, thereby detecting with the detector 9 the X-rays passed through the object inserted in the photographic opening 3. At this time, the X-ray tube 8 and detector 9 are in operation, receiving the electric power supplied from the power unit 10. The transmitted X rays detected by the detector 9 are processed by the signal processing unit 11, which produces image data and transmits the image data to the computer. Then, the computer restructures the image data into an image, thereby providing a tomogram of the object.

As a result of the repetition of the aforementioned photographing process, energy based on back electromotive force during the deceleration of the motor 4 (instructed by the control unit 100 in S1), that is, regenerative energy, is generated in large amounts. The control unit 100 turns on the switch SW1 by throwing the switch to the regenerative resistor 7 side, thereby accumulating the regenerative energy in the charging capacitor 101 (S2).

Thereafter, in a state where the switch SW1 is turned on by being thrown to the motor 4 side (or is turned off by being thrown to the regenerative resistor 7 side), the motor 4 is accelerated (S3), the current detecting unit 102 monitors whether an instantaneous power failure has occurred. When the current detecting unit 102 has detected an instantaneous power failure (S4-Yes), the control unit 100 turns on the switch SW2 (step S5), causing the regenerative energy accumulated in the charging capacitor 101 to be supplied to the motor 4.

In a state where the current detecting unit 102 has detected no instantaneous power failure (S4-No), the control unit 100 keeps the switch SW2 off.

As described above, supplying the regenerative energy accumulated via the regenerative resistor 7 in the charging capacitor 101 again to the power supply system makes it possible to reduce the power consumption without imposing a heavy load on the heat-dissipating structure. Particularly when an instantaneous power failure has occurred, supplying the accumulated regenerative energy to the power supply system enables the motor 4 to be driven stably.

In addition, a part or all of the regenerative energy accumulated via the regenerative resistor in the charging capacitor may be not only supplied to the power supply system but also be used as power for a cooling fan for heat dissipation. By doing this, the regenerative energy can be used again efficiently, thereby improving the heat-dissipation efficiency. An example of this will be explained in a third embodiment of the present invention.

Moreover, when the weight of the rotating frame is large, or when the rotating speed is high, the energy in the deceleration of the rotation becomes large. Therefore, heat dissipation can be reduced by applying the present invention to an X-ray CT apparatus which includes a two-dimensional detector that has columns of heavy detector elements and is rotated together with the X-ray tube at a higher speed than 0.5 sec/revolution.

Furthermore, the X-ray CT apparatus is provided with a capacitor for recovering regenerative energy. Therefore, its regenerative resistor can be made smaller than that of a conventional equivalent, which enables the weight saving of and the downsizing of the apparatus to be realized.

Furthermore, in the invention, the aforementioned configuration may be designed to be a regenerative energy recycling system separate from the X-ray CT apparatus, instead of being incorporated in the X-ray CT apparatus.

Second Embodiment

Next, a second embodiment of the present invention will be explained.

FIG. 7 is a block diagram showing the configuration of the X-ray CT apparatus 1 according to the second embodiment. As shown in FIG. 7, the X-ray CT apparatus 1 comprises a gantry 2 (or body 2) and an information processing unit 30.

The gantry 2, which is configured to collect projection data on a object P, includes a slip ring 21, a motor 4, an X-ray tube 23, an X-ray detector 25, a rotating frame 26, a data collecting unit 27, a noncontact data transfer unit 28, and a regenerated electric power unit 29. The information processing unit 30 generates an X-ray CT image and various pieces of clinical information using the X-ray CT image by controlling the data collecting operation at the gantry 2 and objecting the data collected at the gantry 2 to a specific process. The information processing unit 30 includes a high-voltage generating unit 301, a preprocessing unit 302, a storage unit 303, a restructuring unit 304, an image processing unit 305, a host controller 306, a display unit 307, an input unit 308, and a transmitting and receiving unit 309.

The motor 4 rotates the rotating frame 26. This rotary drive causes the X-ray tube 23 and X-ray detector 25 facing each other to turn on the body axis of the object P in a spiral manner.

The X-ray tube 23, which is a vacuum tube, is provided on the rotating frame 26. To the X-ray tube 23, electric power (tube current, tube voltage) necessary to irradiate X rays is supplied via the slip ring 21 from the high-voltage generating unit 301. The X-ray tube 23 accelerates electrons at the supplied high-voltage and causes them to collide with the target, thereby irradiating X rays to the object placed in the effective field of view FOV.

The detector 25, which is a detector system for detecting the X rays passed through the object, is provided on the rotating frame 26 so as to face the X-ray tube 23. The detector 25 is of the single-slice type or the multi-slice type. A plurality of detecting elements composed of a combination of scintillators and photodiodes are arranged one-dimensionally or two-dimensionally, depending on the type of the detector.

The rotating frame 26, which is a ring to be rotated on the Z-axis, is mounted with the X-ray tube 23 and X-ray detector 25. An opening is made in the midunit of the rotating frame 26. Into the opening part (that is, a photographic opening 3), the object P laid on the couch (not shown) is inserted.

The data collecting unit 27, which is generally called a DAS (data acquisition system), converts the signal output channel by channel from the detector 25 into a voltage signal, amplifies it, and further convents the amplified signal into a digital signal. The resulting data (raw data) is taken in by the information processing unit 30 via the noncontact data transfer unit 28.

The regenerated electric power unit 29 carries out a process related to a regenerative energy recycling function explained later (or a regenerative energy process). Specifically, the regenerated electric power unit 29 accumulates regenerative energy and converts it into heat energy. Moreover, the regenerated electric power unit 29 supplies the accumulated regenerative energy with specific timing to the power supplies corresponding to the motor 4, cooling fan (not shown), the tilt mechanism of the gantry 2, the moving mechanism of the couch on which the object P is laid, the control board built in the table 2, and the like. In the first embodiment, the configuration of FIG. 2 corresponds to the regenerated electric power unit 29. Suppose the regenerated electric power unit 29 of the second embodiment includes the configuration of FIG. 2.

The high-voltage generating unit 301, which is a unit for supplying electric power necessary to irradiate X rays to the X-ray tube 23, is composed of a high-voltage converter, a filament heating converter, a rectifier, and a high-voltage switching unit.

The preprocessing unit 302 receives raw data from the data collecting unit 27 via the noncontact data transfer unit 28 and makes a sensitivity correction or an X-ray intensity correction. The raw data objected to various corrections through 360 degrees is temporarily stored in the storage unit 303. The raw data preprocessed at the preprocessing unit 302 is referred to as "projection data."

The storage unit 303 stores image data, including raw data, projection data, scanogram data, and tomographic data, and programs for inspection plans, and others.

The restructuring unit 304 has a plurality of restructuring methods and restructures image data by the restructuring method selected by the operator.

The image processing unit 305 objects the restructured image data generated by the restructuring unit 304 to image processing for display, such as window conversion or RGB processing, and outputs the result to the display unit 307. Moreover, on the basis of the operator's instruction, the image processing unit 305 generates a pseudo 3D image, such as a tomogram of an arbitrary cross unit, a projected image in an arbitrary direction, or a three-dimensional surface image, and outputs the result to the display unit 307.

The host controller 306 performs overall control of the X-ray CT apparatus 1 in the scanning process, signal processing, image generating process, image displaying process, and the like. For example, in the scanning process, the host controller 306 stores previously input scanning conditions, including the slice thickness, into the memory unit, controls the feed quantity of and feed speed of the high-voltage generating unit 301, couch driving unit 12, and couch top board a along the body axis, the rotating speed of and rotation pitch of the X-ray tube 23 and X-ray detector 25, the irradiating timing of X rays, and the like on the basis of the scanning condition automatically selected according to a patient ID or the like (or the scanning condition directly set at the input unit 308 in the manual mode), and irradiates an X-ray cone beam or an X-ray fan beam to the desired photographic area of the object, thereby carrying out a data collecting (or scanning) process of X-ray CT images.

Moreover, the host controller 306 performs control related to a regenerative energy recycling function explained later.

For example, the host controller 306, when in operation, outputs the rotating speed, rotation start position, and estimated rotation end position of the motor 4 to the control unit 100 with specific timing. The host controller 306 corresponds to the high-order control unit (e.g., see FIG. 2) in the first embodiment.

The display unit 307 is an output unit which displays CT images, including computer tomographic images and scanograms input from the image processing unit 305. Here, a CT value is such that the X-ray absorption coefficient of a substance is represented as a relative value with respect to a reference substance (e.g., water). Moreover, the display unit 307 displays a scanning plan screen or the like realized by a plan support system (not shown).

The input unit 308 is a unit which includes a keyboard, various switches, and a mouse and enables the operator to input various scanning conditions, including a slice thickness and the number of slices.

The transmitting and receiving unit 309 transmits and receives image data, patient information, and the like to and from another apparatus via a network N.

(Regenerative Energy Recycling Function)

Next, the regenerative energy recycling function of the second embodiment will be explained. This function is not only to accumulate regenerative energy in a capacitor but also to convert regenerative energy into heat energy with a regenerative resistor.

Figure 8:
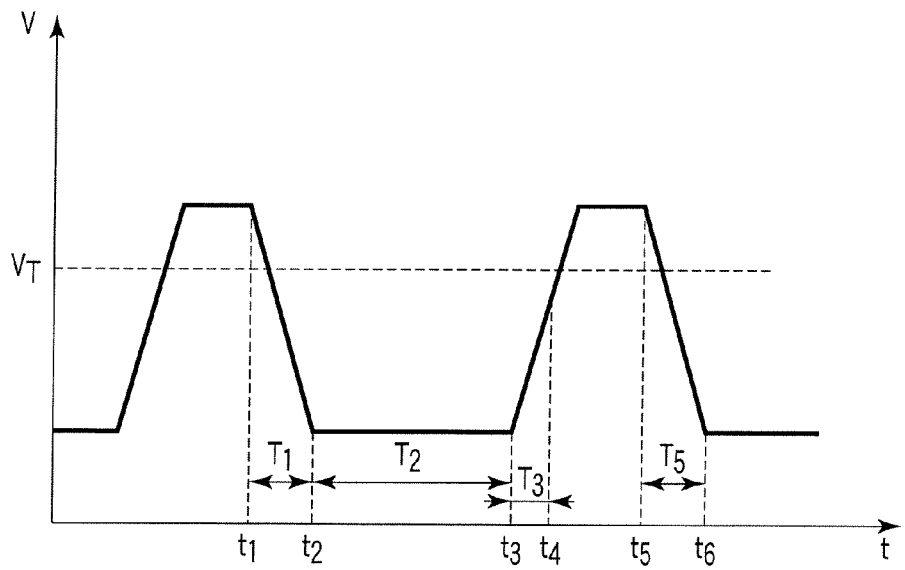
FIG. 8 is a graph showing a temporal change in the rotating speed of the motor 4 in scanning with the X-ray CT apparatus 1.

FIG. 8 is a graph showing a temporal change in the rotating speed of the motor 4 in scanning with the X-ray CT apparatus 1 (that is, the rotating speed of the rotating frame 5 composed of the X-ray tube 23, detector 25, and rotating frame 26). In FIG. 8, regenerative energy is generated in period Ti and in period T5 that the motor 4 decelerates. The control unit 100 monitors a change in the speed of the motor 4. When having detected deceleration start timing (e.g., when having detected an instantaneous power failure in the transmission path between the IGBT and the motor 4), the control unit 100 controls the switch SW2 so that the capacitor 101 and the motor 4 may be electrically connected to each other. As a result, in the capacitor 101, regenerative energy generated during the deceleration of the motor 4 is accumulated.

In addition, the control unit 100 controls the switch SW1 so that the regenerative resistor 7 and the motor 4 may be electrically connected to each other with specific timing after the capacitor 101 starts to accumulate regenerative energy. The regenerative resistor 7 converts regenerative energy generated due to the deceleration of the motor 4 into heat energy and dissipates the heat. The regenerative resistor 7 dissipates the regenerative energy in a specific period, for example, from when the motor starts to decelerate until it starts to accelerate again.

Control of SW1 to connect the regenerative resistor 7 and the motor 4 electrically to each other may be performed after a specific delay time with the deceleration start of the motor 4 as a trigger. Alternatively, control of SW1 may be performed with specific timing, with the electric energy accumulated in the capacitor 104 as a reference (for example, the timing with which the capacitor 101 accumulates electric energy to its full capacity). The timing can be controlled arbitrarily by the setting.

Heat dissipation by the regenerative resistor 7 combined with the regenerative energy recovery by the capacitor 101 is not always needed when the motor 4 is decelerated. Heat dissipation is needed only when regenerative energy cannot be recovered sufficiently by the capacitor 101. Therefore, for example, when the motor 4 is decelerated in the state where its rotating speed has exceeded a specific threshold value VT, or only when the absolute value αT of the roll acceleration has exceeded a specific threshold value, heat may be dissipated by the regenerative resistor 7. Each of the threshold value VT and absolute value αT can be adjusted to an arbitrary value.

(Operation)

Next, the operation in a regenerative energy using process in the X-ray CT apparatus 1 of the second embodiment will be explained.

Figure 9:
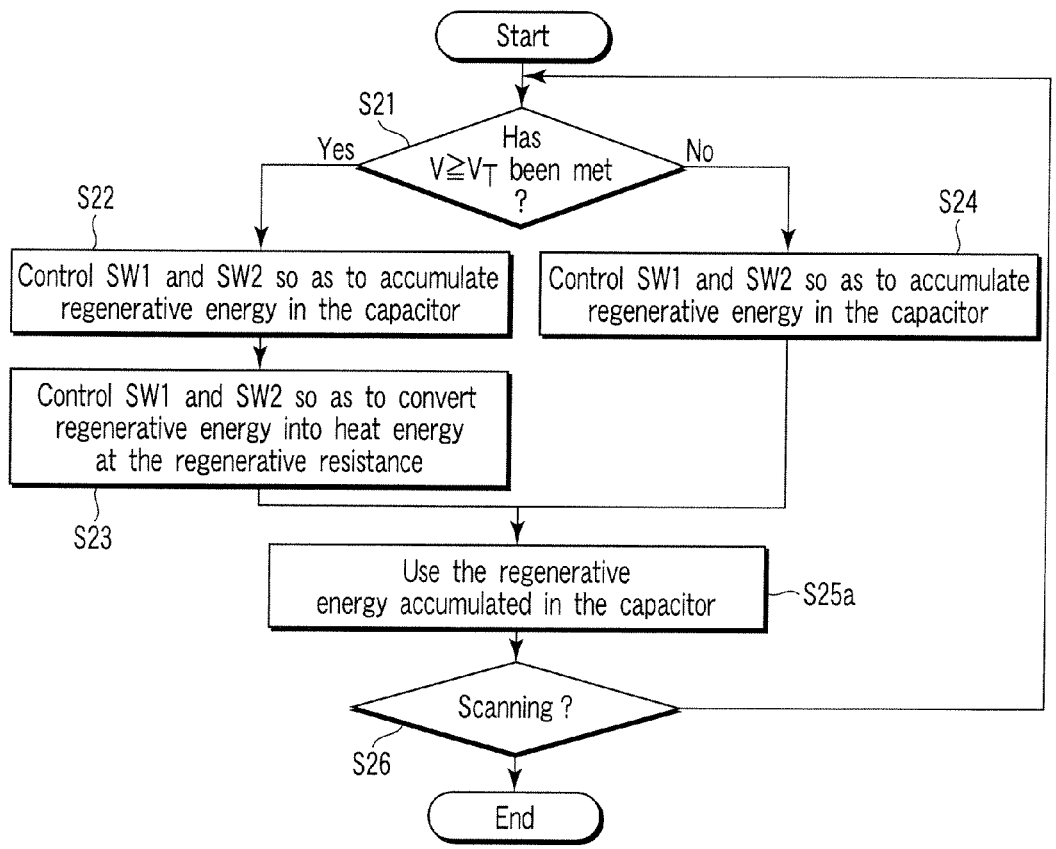
FIG. 9 is a flowchart to help explain the operation in a regenerative energy using process in the X-ray CT apparatus 1.

FIG. 9 is a flowchart to help explain the operation in a regenerative energy using process in the X-ray CT apparatus 1. As shown in FIG. 9, the control unit 100 monitors the rotating speed V of the motor 4 acquired from the host controller 306 and determines whether the speed has exceeded the threshold value VT (step S21). If having determined that the rotating speed V has not exceeded the threshold value VT, the control unit 100 controls the switch SW2 during the deceleration of the motor 4 so that regenerative energy may be accumulated in the capacitor 101 (step S24). The regenerative energy accumulated in the capacitor 101 is supplied, for example, as electric power in accelerating the motor 4 as described in the first embodiment, or as electric power for various units as described in the third and fourth embodiments (step S25*a*).

On the other hand, when having determined that the rotating speed has exceeded the threshold value VT, the control unit 100 not only controls the switch SW2 so that a part of the regenerative energy generated due to the deceleration of the motor 4 may be accumulated in the capacitor 101 but also controls the switch SW1 so that the remaining energy may be dissipated at the regenerative resistor 7 (step 22 and step 23). The regenerative energy accumulated in the capacitor 101 is supplied as electric power to various units, which use the electric power.

Next, a host controller 306 determines whether or not scanning should be carried out continuously. When the scanning is carried out continuously, the process of steps S21 to S25*a* is repeated. Meanwhile, if the scanning is not carried out, the series of regenerative energy recycling process is terminated (step S26).

With the above-described configuration, the following effect can be obtained.

The X-ray CT apparatus of the embodiment makes it possible not only to recover regenerative energy with the capacitor but also to convert regenerative energy into heat energy with the regenerative resistor. Therefore, even when regenerative energy cannot be recovered sufficiently only with the capacitor, regenerative energy generated during deceleration can be dissipated properly outside the apparatus.

Third Embodiment

Next, a third embodiment of the present invention will be explained.

FIG. 10 is a diagram showing the configuration for performing a regenerative energy recycling function according to the third embodiment. As shown in FIG. 10, a regenerated electric power unit 29 and a cooling fan 200 are provided inside a gantry 2 of an X-ray CT apparatus 1.

The regenerated electric power unit 29 includes a switch SW5. The switch SW5 switches the electric connection of a capacitor 101 between the cooling fan 200 and a motor 4.

A control unit 100 controls the switch SW1 and the switch SW5 in a predetermined timing so that the regenerative energy generated due to deceleration of motor 4 may be accumulated in the capacitor 101 or dissipated at a regenerative resistor 7. Further, the control unit 100 controls SW5 in a predetermined timing so that the regenerative energy accumulated in the capacitor 101 is supplied to the power source of a fan.

(Regenerative Energy Recycling Function)

The regenerative energy recycling function according to the present embodiment uses, for example, the regenerative energy collected in the procedures related to the first or second embodiment as the driving electric power for cooling the inside of the apparatus (fan 200 in the present embodiment) in a predetermined timing. Further, to enable specific explanations, the following will be described assuming that the regenerative energy generated due to the deceleration of motor 4 is collected and converted into heat by the procedure of the second embodiment.

The regenerative energy may be supplied to the power source of the cooling fan 200 from the capacitor 101 at any timing excluding the period of accumulating the regenerative energy to the capacitor 101. Accordingly, the control unit 100, for instance, switches the switch SW5 so that the regenerative energy is supplied to the power source of the cooling fan 200 from the capacitor 101 during the acceleration period T3 of the motor 4 shown in FIG. 8. While the regenerative energy is supplied from the capacitor 101, the cooling fan 200 uses such energy as the driving power source. When the regenerative energy supply is terminated, the cooling fan 200 is driven by a usual power source.

(Operation)

Next, the operation in a regenerative energy using process in the X-ray CT apparatus 1 of the present embodiment will be explained.

Figure 11:
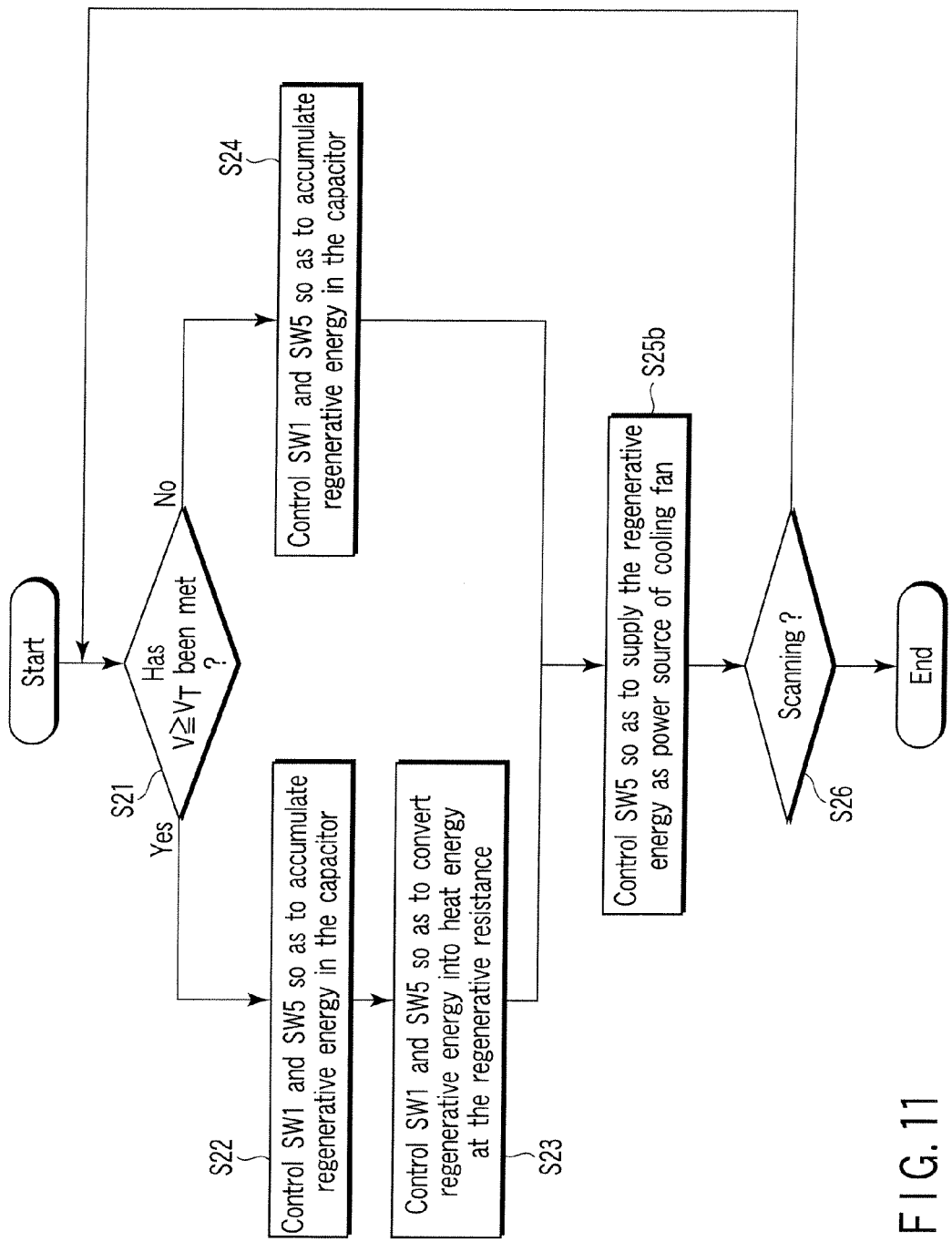
FIG. 11 is a flowchart to help explain the operation in a regenerative energy using process according to the third embodiment.

FIG. 11 is a flowchart to help explain the operation in a regenerative energy using process according to the third embodiment. As shown in FIG. 11, firstly, the regenerative energy is collected and so forth by the capacitor in the same procedure as in the second embodiment (steps S21 to S24).

Next, the control unit 100 switches the switch SW5 to the cooling fan 200 side so that the regenerative energy accumulated in the capacitor 101 is supplied to the power source of the cooling fan 200 during the predetermined period before the start of the next deceleration of the motor 4 (step S25b). As a result, as long as the regenerative energy is supplied from the capacitor 101, the cooling fan 200 is driven by such regenerative energy, using this as its electric power.

Next, a host controller 306 determines whether or not scanning should be carried out continuously. When the scanning is carried out continuously, the process of steps S21 to S25b is repeated. Meanwhile, if the scanning is not carried out, the series of regenerative energy recycling process is terminated (step S26).

With the above-described configuration, the following effect can be obtained.

The X-ray CT apparatus of the present embodiment utilizes the regenerative energy collected by the capacitor as a driving electric power of the cooling fan for cooling the apparatus. Accordingly, while enabling recycling of the regenerative energy, which had conventionally been dissipated, the amount of regenerative energy to be dissipated at the regenerative resistor can be reduced. As a result, the temperature rise inside the apparatus caused by the regenerative energy can be reduced while reducing electric power of the apparatus.

Further, the present X-ray CT apparatus processes the regenerative energy generated upon deceleration of the motor by two systems, which are the cooling fan drive by the regenerative energy and the dissipation by the regenerative resistor. Accordingly, as the regenerative energy dissipated at the regenerative resistor can be reduced, the regenerative resistor can be made smaller in comparison to the past. As a result, a low temperature, downsized and weight saving apparatus can be realized.

Fourth Embodiment

Next, a fourth embodiment of the present invention will be explained.

Figure 12:
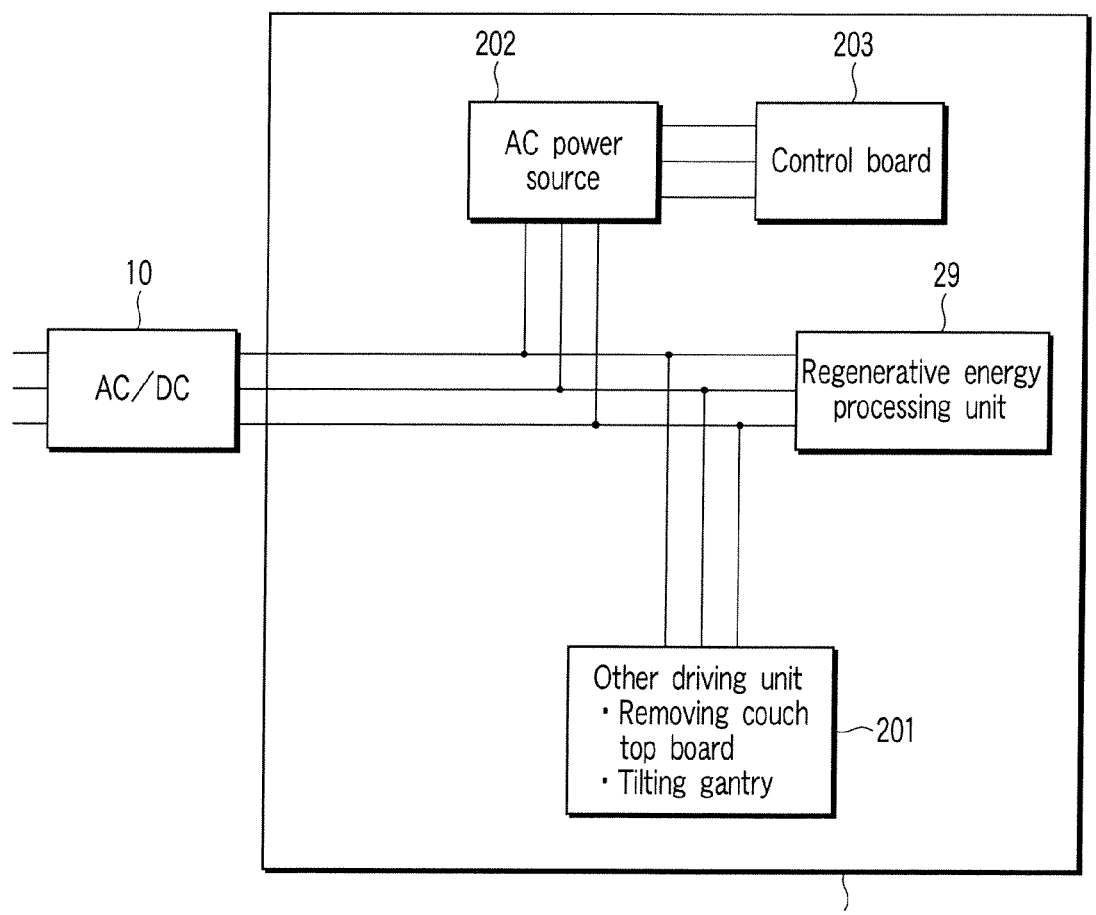
FIG. 12 is a diagram showing the configuration for performing a regenerative energy recycling function according to the forth embodiment.

FIG. 12 is a diagram showing the configuration for performing a regenerative energy recycling function according to the present embodiment.

A regenerated electric power unit 29 possesses the configuration shown in, for example, the third embodiment. There is an electric wiring provided between this regenerated electric power unit 29 and a power source 10 in order to supply a regenerative energy collected at the regenerated electric power unit 29 to the control board 203, which exists in the gantry 2, or other driving units 201 (such as, a driving unit to move a couch top board to the left, right, top and bottom, a driving unit to tilt a gantry 2 and so forth).

(Regenerative Energy Recycling Function)

The regenerative energy recycling function of the present embodiment uses, for example, the regenerative energy collected by the means of the first or second embodiment, for the control board in the gantry 2, for removing the couch top board, for tilting the gantry 2 and so forth. Further, to enable specific explanations, the following will be described assuming that the regenerative energy generated due to the deceleration of motor 4 is collected and converted into heat by the procedure of the second embodiment.

When the regenerative energy is accumulated in a capacitor 101, the control unit 100 controls a switch SW1 and so forth in order to supply the regenerative energy to other driving units 201 or to a control board 203 as an electric power at a predetermined timing. In other words, for instance, if the couch top board is instructed to move during the period T2 shown in FIG. 8, the control unit 100 switches SW5 to the driving unit 201 side while turning off the switch SW1 so that the regenerative energy is supplied to the power source of a moving mechanism of the couch from the capacitor 101. As long as the regenerative energy is supplied from the capacitor 101, the other driving units 201 uses the energy as the driving power source. When the regenerative energy supply is terminated, the other driving units 201 is driven by a usual AC power source 202.

(Operation)

Next, the operation in a regenerative energy using process in the X-ray CT apparatus 1 of the present embodiment will be explained.

Figure 13:
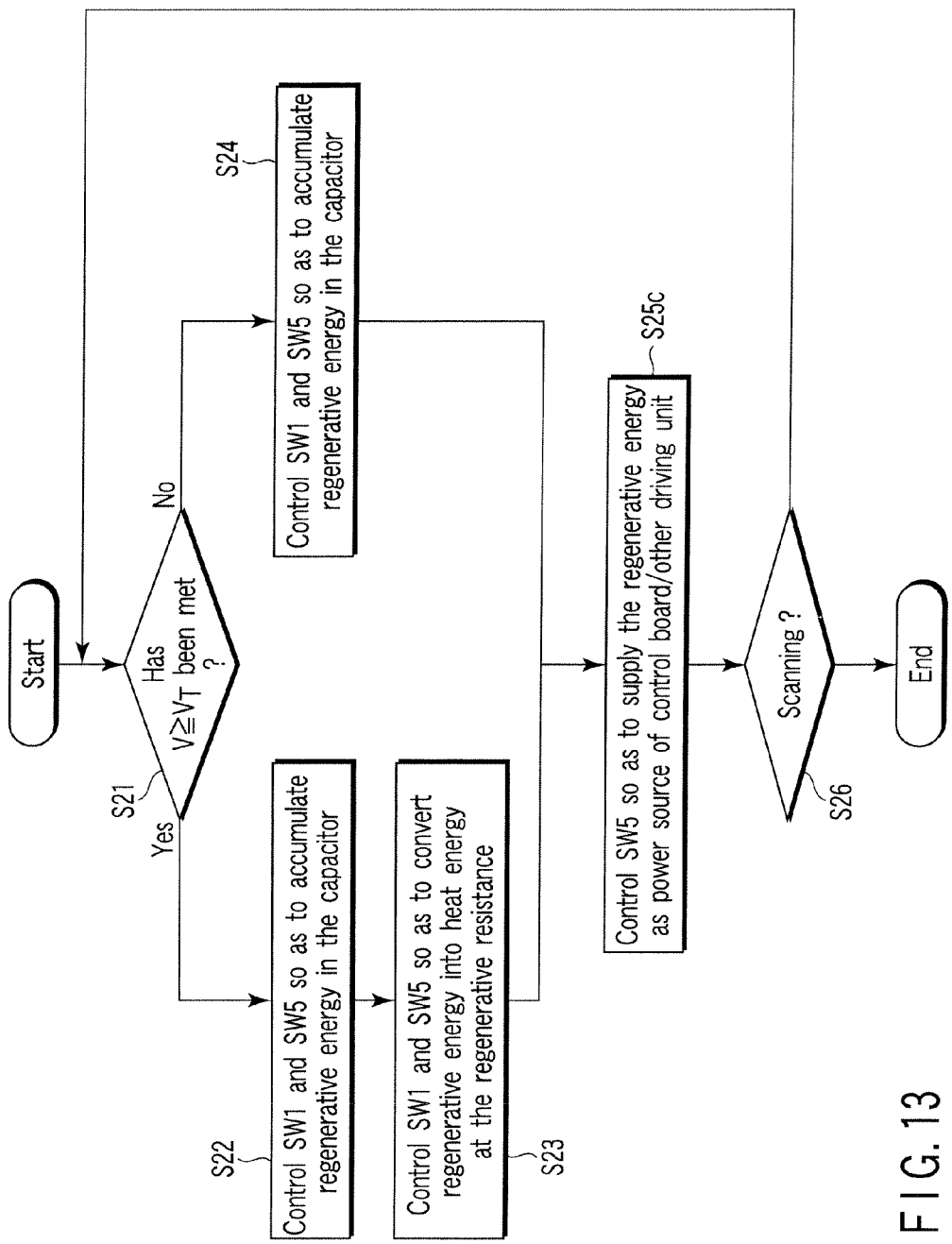
FIG. 13 is a flowchart to help explain the operation in a regenerative energy using process according to the forth embodiment.

FIG. 13 is a flowchart to help explain the operation in a regenerative energy using process according to the fourth embodiment. As shown in FIG. 13, firstly, the regenerative energy is collected and so forth by the capacitor in the same procedure as in the second and third embodiments (steps S21 to S24)

Next, the control unit 100 controls switches SW1 and SW5 so that the regenerative energy accumulated in the capacitor 101 during a predetermined period (for example, period T2) is supplied to the other driving units 201 or the power source of control board 203 (step S25c). As a result, as long as the regenerative energy is supplied from the capacitor 101, each device provided on the control board, or couch, gantry and so forth is driven by the regenerative energy, using this as the electric power.

Next, a host controller 306 determines whether or not scanning should be carried out continuously. When scanning is carried out continuously, the process of steps S21 to S25c is repeated. Meanwhile, if scanning is not carried out, the series of regenerative energy recycling process is terminated (step S26).

With the above-described configuration, the following effect can be obtained.

The X-ray CT apparatus of the present embodiment utilizes the regenerative energy collected by the capacitor as an electric power of other drive systems (such as, moving the couch, tilting the gantry and so forth) or the control board, which are equipped by the apparatus. Accordingly, while enabling recycling of the regenerative energy, which had conventionally been dissipated, the amount of regenerative energy to be dissipated at the regenerative resistor can be reduced. As a result, the temperature rise inside the apparatus caused by the regenerative energy can be reduced while reducing electric power of the apparatus.

Further, the present X-ray CT apparatus processes the regenerative energy generated upon deceleration of the motor by two systems, which are such as moving the couch by the regenerative energy and the dissipation by the regenerative resistor. Accordingly, as the regenerative energy dissipated at the regenerative resistor can be reduced, the regenerative resistor can be made smaller in comparison to the past. As a result, a low temperature, downsized and weight saving apparatus can be realized.

Further, the present invention is not limited to the original embodiments above and can be materialized by modifying the components within the range of the summary in the execution phase. Specific examples are as follows:

(1) Each embodiment of the present invention does not dwell on the capacity of the capacitor for collecting the regenerative energy. As a preferred example, a capacity, which enables accumulation of several-fold amount of energy to put the motor 4 in a stopped state from a rotational state, can be adopted.

(2) By combining the third and fourth embodiments, the regenerative energy collected by the capacitor may, for instance, also be distributed to each power source of the cooling fan, other drive systems or control board according to need.

This invention is not limited to the above embodiments and may be practiced or embodied in still other ways without departing from the spirit or essential character thereof. In addition, various inventions may be formed by combining a plurality of component elements disclosed in the embodiments. For instance, some component elements may be removed from all of the component elements disclosed in the embodiments. Moreover, component elements used in two or more embodiments may be combined suitably.

What is claimed is:

1. An X-ray computer tomographic imaging apparatus, comprising:
   a rotating frame including an X-ray generating unit configured to irradiate X rays and an X ray detecting unit configured to detect X rays, said rotating frame configured to rotate around a predetermined axis;
   a first driving unit configured to drive the rotating frame rotationally;
   a power source configured to provide electric power to the first driving unit; and
   a regenerated electric power unit configured to accumulate regenerative energy generated when the rotating speed of the rotating frame is decelerated.

2. The X-ray computer tomographic imaging apparatus according to claim 1, wherein the regenerated electric power unit includes:
   a capacitor configured to accumulate the regenerative energy;
   a first switch configured to switch an electric connection between the first driving unit and the capacitor; and
   a control unit configured to control the first switch to connect the capacitor to the first driving unit electrically when the rotating speed of the rotating frame is decelerated.

3. The X-ray computer tomographic imaging apparatus according to claim 2, wherein the regenerated electric power unit includes:
   a resistor configured to convert the regenerative energy into heat energy; and
   a second switch configured to switch an electric connection between the first driving unit and the resistor,
   wherein the control unit is further configured to control the second switch to connect the resistor to the first driving unit electrically at a predetermined timing.

4. The X-ray computer tomographic imaging apparatus according to claim 3, wherein the control unit is further configured to control the second switch to connect the resistor to the first driving unit when the accumulating of the regenerative energy to the capacitor is completed.

5. The X-ray computer tomographic imaging apparatus according to claim 2, further comprising:
   a second switch configured to switch an electric connection between the capacitor and a cooling unit configured to cool the X-ray computer tomographic imaging apparatus,
   wherein the control unit is further configured to control the second switch to connect the capacitor to the cooling unit electrically at a predetermined timing.

6. The X-ray computer tomographic imaging apparatus according to claim 5, further comprising:
   a detection unit configured to detect electric power to be supplied to the first driving unit,
   wherein the control unit is further configured to control the first switch when the detection unit detects an instantaneous power failure.

7. The X-ray computer tomographic imaging apparatus according to claim 2, further comprising:
   a second switch configured to switch an electric connection between the capacitor and at least one of a second driving unit, a third driving unit and a control board, the second driving unit being configured to tilt a gantry which includes the rotating frame and the first driving unit, the third driving unit being configured to move a coach top board to place an object to be examined and the control board being arranged in the gantry,
   wherein the control unit is further configured to control the second switch to connect the capacitor to at least one of the second driving unit, the third driving unit and the control board electrically at a predetermined timing.

8. The X-ray computer tomographic imaging apparatus according to claim 7, further comprising:
   a detection unit configured to detect electric power to be supplied to the first driving unit,
   wherein the control unit is further configured to control the first switch when the detection unit detects an instantaneous power failure.

9. The X-ray computer tomographic imaging apparatus according to claim 2, further comprising:
   a detection unit configured to detect electric power to be supplied to the first driving unit,
   wherein the control unit is further configured to control the first switch when the detection unit detects an instantaneous power failure.

10. A control method of an X-ray computer tomographic imaging apparatus, comprising:
- driving a rotational body rotationally around a predetermined axis, the rotational body including an X-ray generating unit to irradiate X rays and an X ray detecting unit to detect X rays; and
- accumulating regenerative energy generated when the rotating speed of the rotational body is decelerated.

11. The control method according to claim 10, further comprising:
- connecting a capacitor configured to accumulate the regenerative energy in a driving unit configured to drive the rotational body when the rotating speed of the rotational body is decelerated.

12. The control method according to claim 11, further comprising:
- connecting a resistor configured to convert the regenerative energy into heat energy in the driving unit when the accumulating of the regenerative energy to a capacitor is completed.

13. The control method according to claim 12, further comprising:
- connecting the capacitor to a cooling unit configured to cool the X-ray computer tomographic imaging apparatus when a detection unit configured to detect electric power to be supplied to the driving unit detects an instantaneous power failure.

14. The control method according to claim 11, further comprising:
- connecting the capacitor to at least one of a second driving unit, a third driving unit and a control board, the second driving unit being configured to tilt a gantry which includes the rotational body and the first driving unit, the third driving unit being configured to move a coach top board to place an object to be examined and the control board being arranged in the gantry, in a predetermined timing.

15. The control method according to claim 14, further comprising:
- connecting the capacitor to at least one of the second driving unit, the third driving unit and the control board when a detection unit configured to detect electric power to be supplied to the driving unit detects an instantaneous power failure.

16. The control method according to claim 10, further comprising:
- connecting a resistor configured to convert the regenerative energy into heat energy in a driving unit configured to drive the rotational body, in a predetermined timing.

17. The control method according to claim 16, further comprising:
- connecting the resistor configured to convert the regenerative energy into heat energy in the driving unit when the accumulating of the regenerative energy to the capacitor is completed.

18. The control method according to claim 16, further comprising:
- connecting the resistor configured to convert the regenerative energy into heat energy in the driving unit when a detection unit configured to detect electric power to be supplied to the driving unit detects an instantaneous power failure.

* * * * *